(12) United States Patent
Suzuki et al.

(10) Patent No.: US 8,303,607 B2
(45) Date of Patent: Nov. 6, 2012

(54) MEDICAL DEVICE

(75) Inventors: Yutaka Suzuki, Nasushiobara (JP); Hideaki Matsunami, Akita (JP); Yukihiko Sakaguchi, Akita (JP); Masao Ikeda, Akita (JP); Yasunori Kojo, Akita (JP)

(73) Assignees: Yutaka Suzuki, Tokyo (JP); Sumitomo Bakelite Co., Ltd., Tokyo (JP)

( * ) Notice: Subject to any disclaimer, the term of this patent is extended or adjusted under 35 U.S.C. 154(b) by 297 days.

(21) Appl. No.: 12/677,025

(22) PCT Filed: Sep. 26, 2008

(86) PCT No.: PCT/JP2008/002683
§ 371 (c)(1),
(2), (4) Date: Mar. 8, 2010

(87) PCT Pub. No.: WO2009/041057
PCT Pub. Date: Apr. 2, 2009

(65) Prior Publication Data
US 2010/0191259 A1 Jul. 29, 2010

(30) Foreign Application Priority Data
Sep. 26, 2007 (JP) ................................. 2007-248375

(51) Int. Cl.
*A61B 17/04* (2006.01)
(52) U.S. Cl. .................. 606/144; 606/139; 606/148
(58) Field of Classification Search .................. 606/139, 606/144–148, 130, 96, 186; 112/169; 604/116, 604/170.02, 174
See application file for complete search history.

(56) References Cited

U.S. PATENT DOCUMENTS

| | | | | |
|---|---|---|---|---|
| 4,058,114 A | * | 11/1977 | Soldner | 600/461 |
| 4,586,490 A | * | 5/1986 | Katz | 600/3 |
| 5,052,396 A | * | 10/1991 | Wedel et al. | 600/461 |

(Continued)

FOREIGN PATENT DOCUMENTS
JP 57-49440 3/1982
(Continued)

OTHER PUBLICATIONS

International Search Report for International Application No. PCT/JP2008/002683 mailed Dec. 9, 2008.

*Primary Examiner* — Corrine M McDermott
*Assistant Examiner* — Todd J Scherbel
(74) *Attorney, Agent, or Firm* — Smith, Gambrell & Russell, LLP

(57) ABSTRACT

A medical device includes a main body elongated in a vertical direction. A guide section protrudes from a lower end of the main body in a direction crossing the vertical direction and includes first and second guide holes. A first unit includes a first puncture needle slidably supported by the main body near an upper end of the first puncture needle in the vertical direction and having a sharp lower end slidably inserted into the first guide hole from above. The first unit has a first holding plate integrally fixed to the first puncture needle. A second unit includes a second puncture needle slidably inserted into the second guide hole from above and a second holding plate integrally fixed to the second puncture needle. The second holding plate separably abuts on the first holding plate from above. A position of the second guide hole is selectable along the guide section.

11 Claims, 20 Drawing Sheets

U.S. PATENT DOCUMENTS

| | | | |
|---|---|---|---|
| 5,098,383 A * | 3/1992 | Hemmy et al. | 604/116 |
| 5,141,513 A * | 8/1992 | Fortune et al. | 606/96 |
| D354,810 S * | 1/1995 | Nazre | D24/140 |
| D357,534 S * | 4/1995 | Hayes | D24/140 |
| 5,403,322 A * | 4/1995 | Herzenberg et al. | 606/98 |
| 5,507,755 A * | 4/1996 | Gresl et al. | 606/139 |
| 5,722,981 A * | 3/1998 | Stevens | 606/148 |
| 6,066,142 A * | 5/2000 | Serbousek et al. | 606/96 |
| 6,485,426 B2 * | 11/2002 | Sandhu | 600/461 |
| 6,506,182 B2 * | 1/2003 | Estabrook et al. | 604/164.11 |
| 7,320,693 B2 * | 1/2008 | Pollack et al. | 606/144 |
| 7,615,062 B2 * | 11/2009 | Deland | 606/148 |
| 7,753,935 B2 * | 7/2010 | Brett et al. | 606/213 |
| 2004/0267164 A1 * | 12/2004 | Rhodes et al. | 600/587 |
| 2006/0069398 A1 * | 3/2006 | Suzuki et al. | 606/148 |
| 2007/0282351 A1 * | 12/2007 | Harada et al. | 606/138 |
| 2009/0264905 A1 * | 10/2009 | Funada | 606/146 |

FOREIGN PATENT DOCUMENTS

| | | |
|---|---|---|
| JP | 4-226643 | 8/1992 |
| JP | 2007-82827 | 4/2007 |
| JP | 2007-151615 | 6/2007 |

* cited by examiner

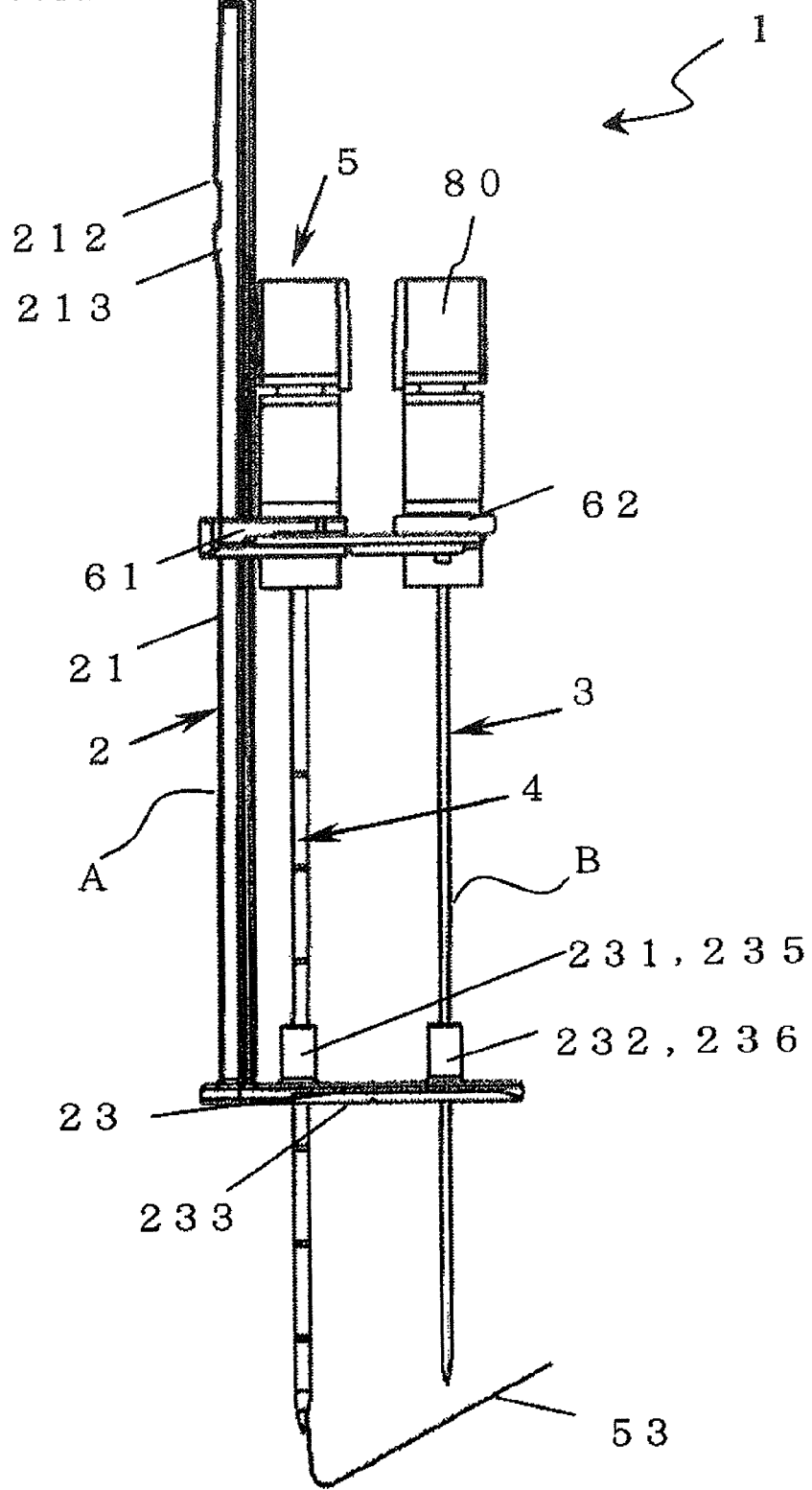

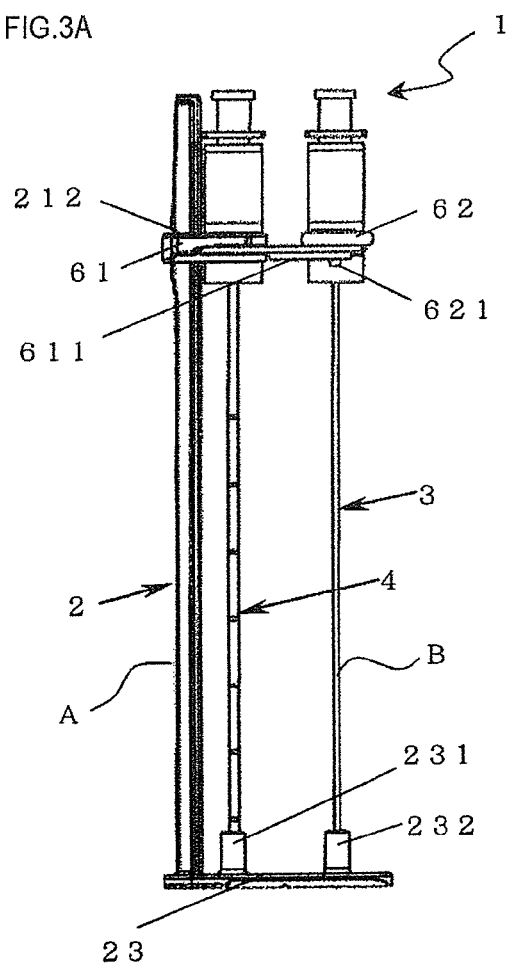
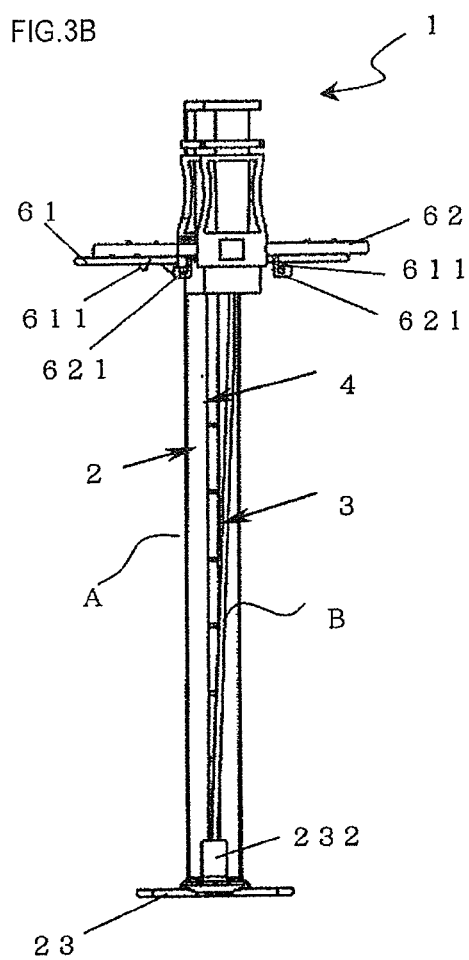

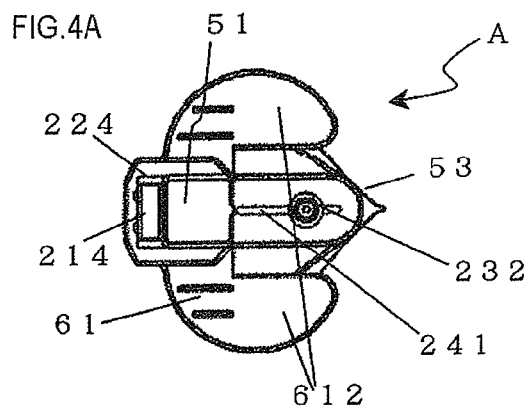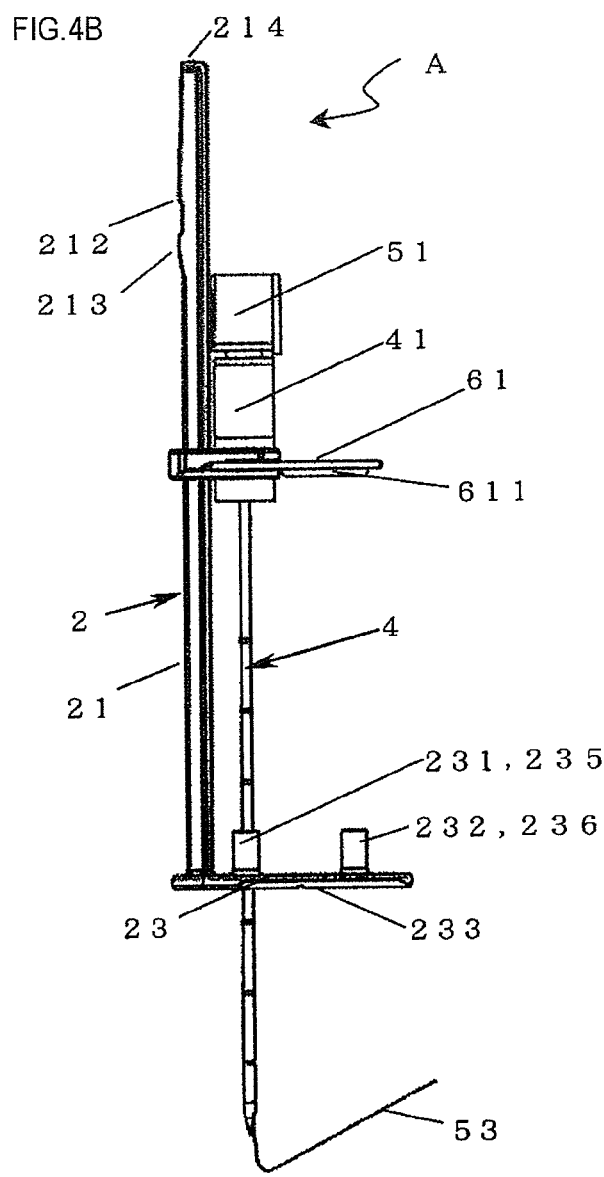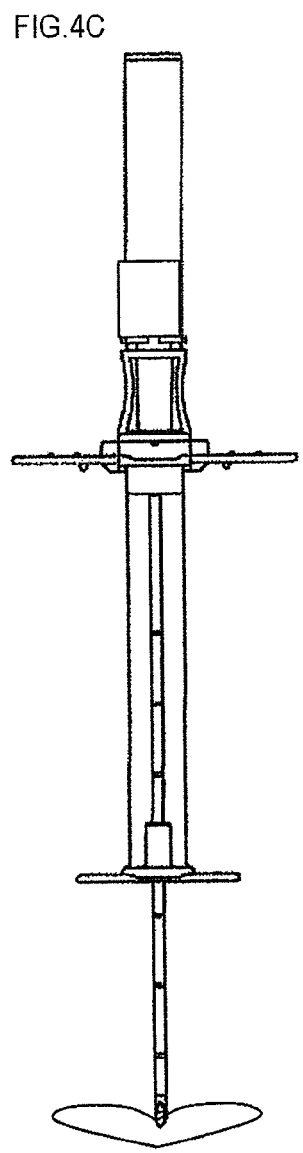

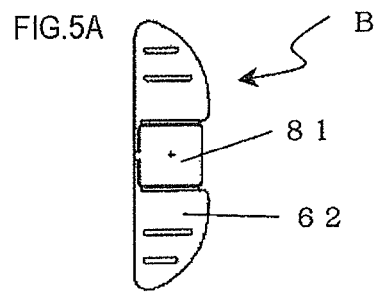
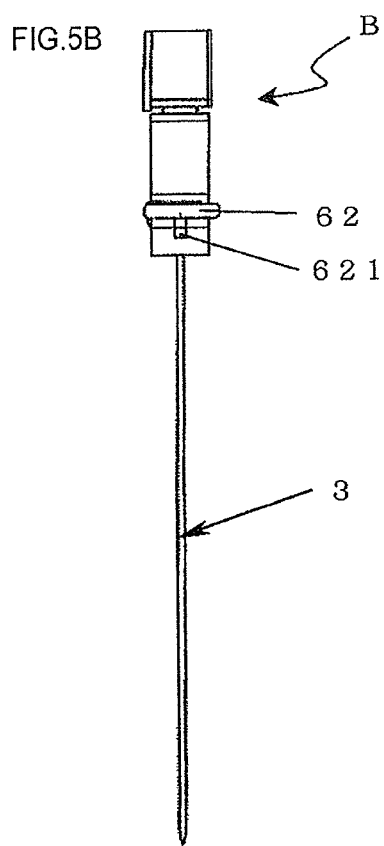
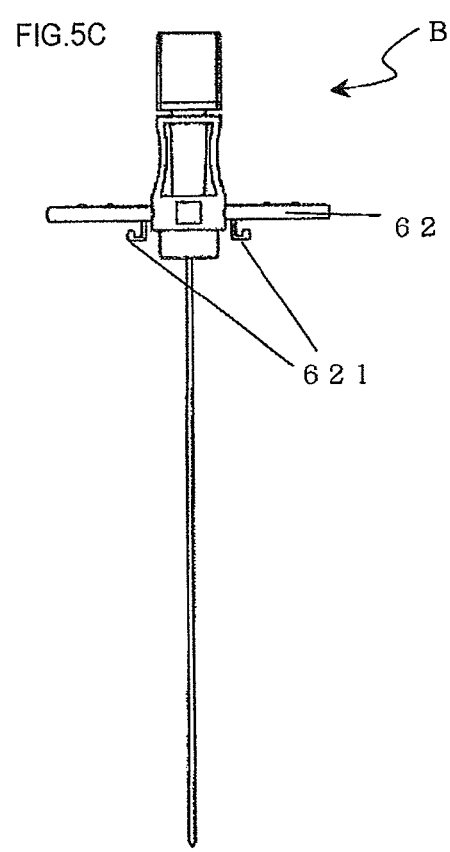

MEDICAL DEVICE

TECHNICAL FIELD

The present invention relates to a medical device employed to suturing and securing an internal tissue of a living body to a body surface.

BACKGROUND ART

Three types of nutrition feeding methods, that is, intravenous feeding, gastric feeding by insertion of a tube from a patient's nose into his or her stomach or the like, and enteral feeding from a gastric fistula are executed for a patient unable to take nourishment from a mouth.

In recent years, following development of enteral nutrition supplements and the enteral feeding therefor, enteral nutrition management based on PEG (Percutaneous Endoscopic Gastrostomy) has frequently been made.

At the time of gastrostomy, it is necessary to form a through-hole penetrating through the abdominal wall and gastric wall of a patient as a pretreatment. Prior to formation of the through-hole, the following procedures are normally carried out. Two puncture needles are put into the stomach from outside the patient's body so as to temporarily fix the mobile gastric wall, a suture is inserted into the stomach through within one of the two puncture needles, and the suture is pulled out to the outside of the body through the other puncture needle, thereby suturing the abdominal wall to the gastric wall.

As medical devices for such suture, there is disclosed, for example, a medical device configured to include a puncture needle for inserting a suture ("suture insertion needle"), a puncture needle for grasping the suture ("suture-grasping needle") arranged in parallel to the suture-insertion needle, a stylet slidably inserted into the suture-grasping needle, and a fixing member fixing the suture-insertion needle and the suture-grasping needle on their distal ends (see, for example, Patent Document 1).

Patent Document 1: Japanese Patent Application Laid-Open No. 04-226643

DISCLOSURE OF THE INVENTION

However, the medical device described in the Patent Document 1 has the following problem. It is disadvantageously necessary to decide piercing positions of the two puncture needles in advance since the two puncture needles should be inserted simultaneously.

Furthermore, in the medical device described in the Patent Document 1, a distance between the two puncture needles cannot be changed since the fixing member fixes the two puncture needles on their proximal ends, which disadvantageously restricts selection of the piercing positions.

The present invention has been made in view of the above circumstances. It is an object of the present invention to provide a medical device capable of arbitrarily selecting piercing positions of two puncture needles and performing suturing a body surface part to an internal tissue at an optimum position.

The present invention described in the following (1) to (13) can attain such an object:

(1) A medical device including:
a main body elongated in a vertical direction;
a guide section protruding from a lower end of the main body in a direction crossing the vertical direction, and including a first guide hole and a second guide hole penetrating through the guide section in the vertical direction;
a first unit including a first puncture needle of a hollow structure and a first holding plate, the first puncture needle being slidably supported by the main body near an upper end of the first puncture needle in the vertical direction and having a sharp lower end slidably inserted into the first guide hole from above, the first holding plate being integrally fixed to neighborhoods of the upper end of the first puncture needle; and
a second unit including a second puncture needle of the hollow structure and a second holding plate, the second puncture needle having a sharp lower end slidably inserted into the second guide hole from above, the second holding plate being integrally fixed to neighborhoods of an upper end of the second puncture needle,
wherein the first unit and the second unit are formed separately,
the second holding plate for the second puncture needle inserted into the second guide hole separably abuts on the first holding plate for the first puncture needle from above, and
a position of the second guide hole with respect to the first guide hole is selectable along the guide section.

(2) The medical device according to (1), wherein a slider including the second guide hole is slidable along the guide section.

(3) The medical device according to (2),
wherein the slider slides within a sliding range including at least a region where a distance between a central portion of the second guide hole and a central portion of the first guide hole is equal to or larger than 5 mm and equal to or smaller than 25 mm.

(4) The medical device according to (2) or (3),
wherein the guide section includes a slide groove slidably supporting the slider.

(5) The medical device according to any one of (2) to (4),
wherein the guide section includes fixing unit for fixing the slidable slider.

(6) The medical device according to any one of (1) to (5), including
a connector separably connecting the first holding plate to the second holding plate,
wherein the first puncture needle and the second puncture needle do not overlap at least partially when the first puncture needle is viewed in a direction connecting the second guide hole to the first guide hole in a state of connecting the first holding plate to the second holding plate by the connector.

(7) The medical device according to (1),
wherein the guide section includes at least the two second guide holes different from each other in a distance to the first guide hole.

(8) The medical device according to (1) or (7),
wherein a distance between the first puncture needle and the second puncture needle on the first or second holding plate is smaller than a distance between the first puncture needle in the first guide hole and the second puncture needle in the second guide hole located at a closest position to the first guide hole in a state of connecting the first holding plate to the second holding plate.

(9) The medical device according to any one of (1) to (8),
wherein a scale indicating a distance between the first puncture needle inserted into the first guide hole and the second puncture needle inserted into the second guide hole on the guide section is printed on one of surfaces of the guide section.

(10) The medical device according to any one of (1) to (9), wherein the guide section includes a cylindrical first accommodation section having the first guide hole formed therein; and a cylindrical second accommodation section having the second guide hole formed therein, the main body includes a locking section, the first puncture needle being locked to the locking section in a state of accommodating a tip of the first puncture needle in the first accommodation section, and a tip of the second puncture needle connected to the first puncture needle locked to the locking section is accommodated in the second accommodation section.

(11) The medical device according to (10), wherein a slide hole for slidably moving the first unit and the main body with respect to each other is formed in the first holding plate, the locking section is formed on the main body as a concave portion, the first holding plate sliding in the slide hole being locked to the concave portion.

(12) The medical device according to any one of (1) to (11), further including a suture traction tool, wherein the suture traction tool includes:

a rod section slidably arranged within the first puncture needle;

a handle section formed integrally on an upper end of the rod section, and located upward of the upper end of the first puncture needle; and an annular section formed integrally on a lower end of the rod section, and protruding or retracting from the lower end of the first puncture needle.

(13) The medical device according to (12), wherein a distance from a longitudinal axis of the rod section is printed on the annular section.

While the vertical direction is defined in the present invention, the vertical direction is defined for sake of convenience so as to briefly describe a relative relation among constituent elements of the present invention and the direction is not intended to limit a direction during manufacturing or using the present invention if the present invention is carried out.

Furthermore, in the present invention, "a position of a guide hole inserted into a puncture needle" comprehends an instance in which the position of the guide hole is continuously movable and an instance in which an arbitrary one of a plurality of guide holes is selected and in which the puncture needle is inserted into the selected guide hole.

Moreover, various constituent elements of the present invention are not necessarily present independently of one another but a plurality of constituent elements may be formed as one member, one constituent element may be formed to include a plurality of members, a certain constituent element is a part of another constituent element, a part of a certain constituent element overlaps a part of another constituent element or the like. For example, the guide section may be formed to include a plurality of members. Alternatively, the first or second accommodation section and the slider may be formed as one member.

The present invention can provide a medical device capable of arbitrarily selecting piercing positions of two puncture needles and performing suture of a body surface part to an internal tissue at an optimum position.

BRIEF DESCRIPTION OF THE DRAWINGS

FIG. 2 is a front view of the medical device.

FIG. 3A is a front view showing a state in which tips of puncture needles of the medical device are accommodate into a main body, and FIG. 3B is a right side view showing the state.

FIG. 4A is a top view showing a state in which a main body, a first puncture needle, a first holding plate, and a suture traction tool are assembled together, FIG. 4B is a front view showing the state, and FIG. 4C is a right side view showing the state.

FIG. 5A is a top view showing a state in which a second puncture needle is fitted into a second holding plate, FIG. 5B is a front view showing the state, and FIG. 5C is a right side view showing the state.

BEST MODE FOR CARRYING OUT THE INVENTION

Figure 1A:
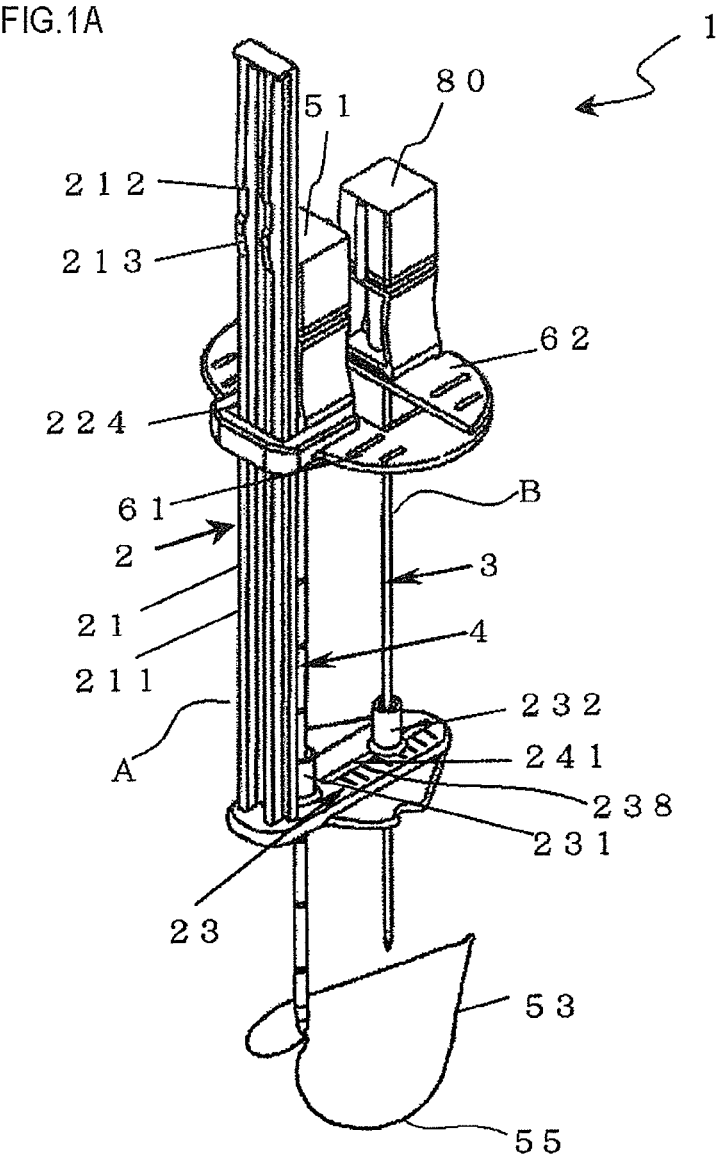
FIG. 1A is a perspective view showing an example of a medical device according to the present invention and FIG. 1B is a top view of the medical device.

Preferred embodiments of the present invention will be described hereinafter with reference to the drawings while taking a medical device used for suturing a body surface part to an internal tissue by a suture as an example.

In all the drawings, common constituent elements are denoted by the same reference symbols and are not described in detail. Further, in the drawings, an upper side is assumed as a proximal end side and a lower side is assumed as a tip side.

Figure 1B:
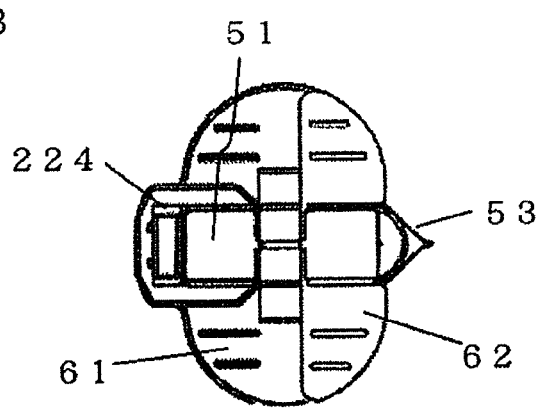
Figure 6A:
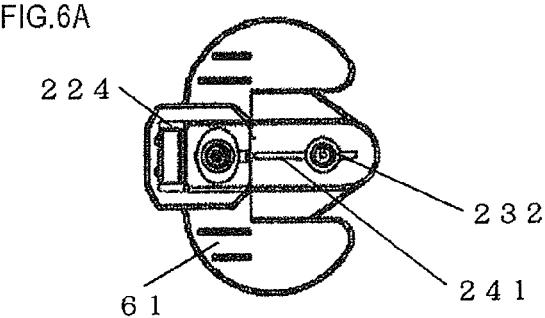
FIG. 6A is a top view showing a state in which the main body, the first puncture needle, and the first holding plate are assembled together.
Figure 6B:
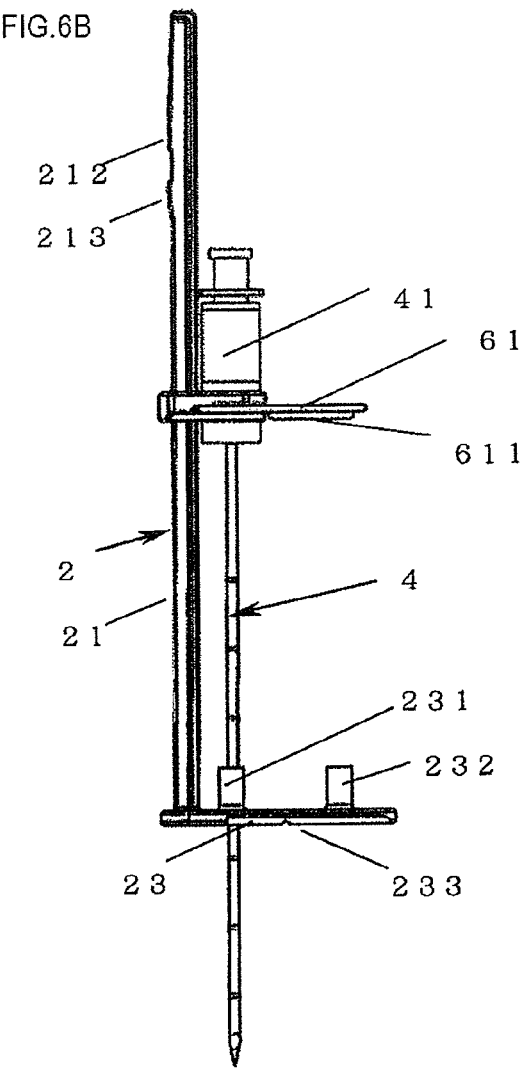
FIG. 6B is a front view showing the state.
Figure 6C:
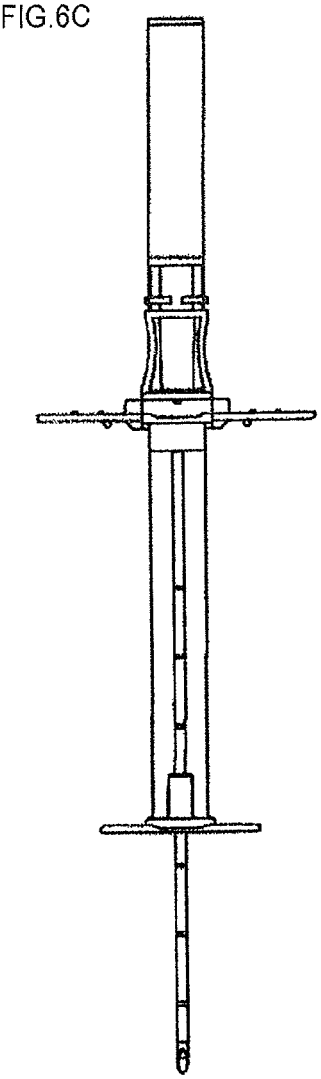
FIG. 6C is a right side view showing the state.
Figure 7:
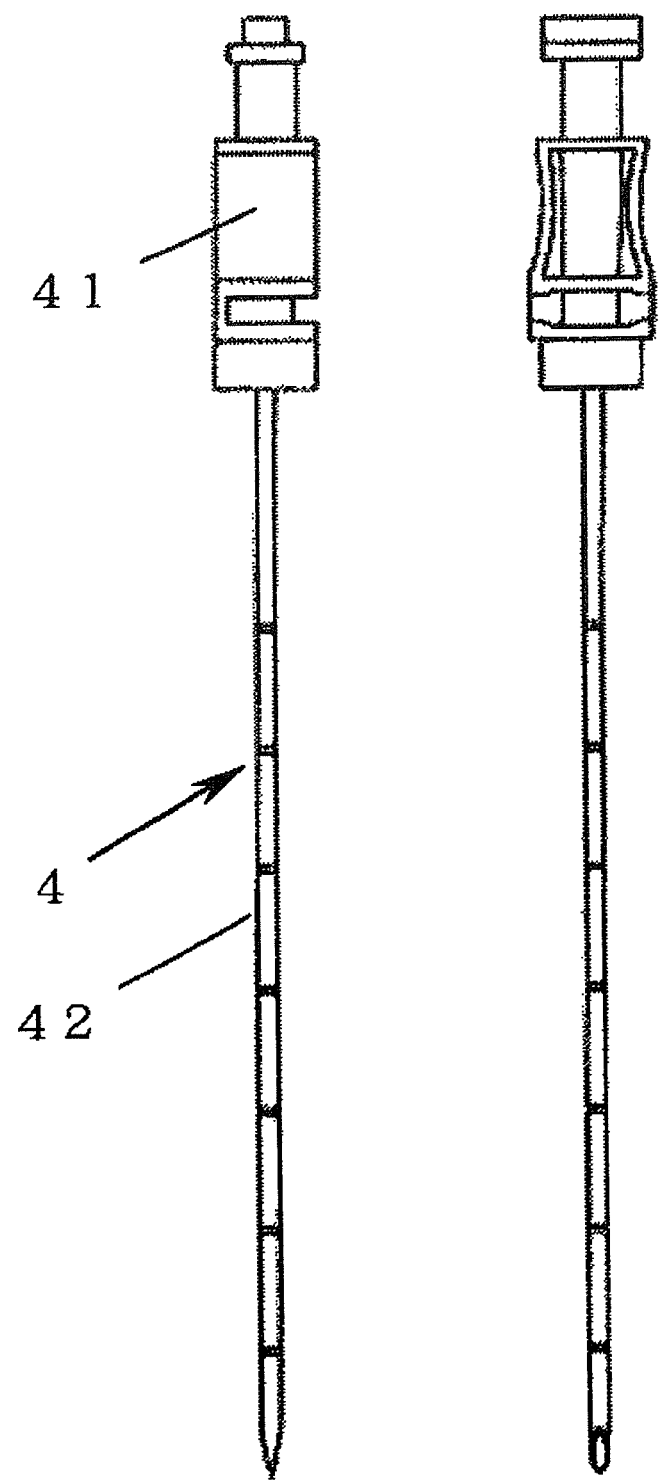
FIG. 7 is a front view and a right side view of the first puncture needle.

FIG. 1A is a perspective view showing a medical device according to an embodiment of the present invention. FIG. 1B is a top view of the medical device.

As shown in FIGS. 1 to 18, a medical device 1 according to this embodiment includes a first unit A and a second unit B, and the first unit A and the second unit B are formed separately and detachably from each other.

As shown in FIG. 4, the first unit A includes a main body 2 elongated in a vertical direction, and an accommodation section 23 that serves as a guide section protruding from a lower end of the main body 2 in a direction crossing the vertical direction. A first guide hole 235 and a second guide hole 236 a position of which is selectable and which is provided along the accommodation section 23 (guide section) are provided to penetrate through the accommodation section 23 in the vertical direction.

The first unit A also includes a first puncture needle 4 of a hollow structure and a first holding plate 61 fixed integrally to neighborhoods of an upper end of the first puncture needle 4. The main body 2 slidably supports the first puncture needle 4 near the upper end of the first puncture needle 4, and a sharp lower end of the first puncture needle 4 is slidably inserted into the first guide hole 235 from above.

In this embodiment, the accommodation section 23 protrudes in a direction orthogonal to the vertical direction in which the main body 2 extends.

The accommodation section 23 is a plate-shaped and a perpendicular direction to a plate surface of the accommodation section 23 coincides with the vertical direction in which the main body 2 extends. That is, the accommodation section 23 is provided to protrude in a horizontal direction if the main body 2 is assumed in the perpendicular direction.

A direction connecting the first guide hole 235 to the second guide hole 236 is referred to as the "horizontal direction" among in-plane directions of the accommodation section 23, irrespectively of a direction of gravity, hereinafter unless specified otherwise.

A position of the second guide hole 236 is selected to be in a direction along the accommodation section 23 (guide section). This direction may be either identical to or different from a direction in which the accommodation section 23 protrudes.

The position of the second guide hole 236 may be adjustable continuously or one of a plurality of second guide holes 236 may be selected to insert a second puncture needle 3 into the selected second guide hole 236. In this embodiment shown in FIG. 4, a second accommodation section 232 that includes the second guide hole 236 and that is a slider is slidable along the accommodation section 23.

As shown in FIGS. 2 and 5, the second unit B includes the second puncture needle 3 of a hollow structure having a sharp lower end slidably inserted into the second guide hole 236 from above, and a second holding plate 62 fixed integrally to neighborhoods of the second puncture needle 3.

Figure 11:
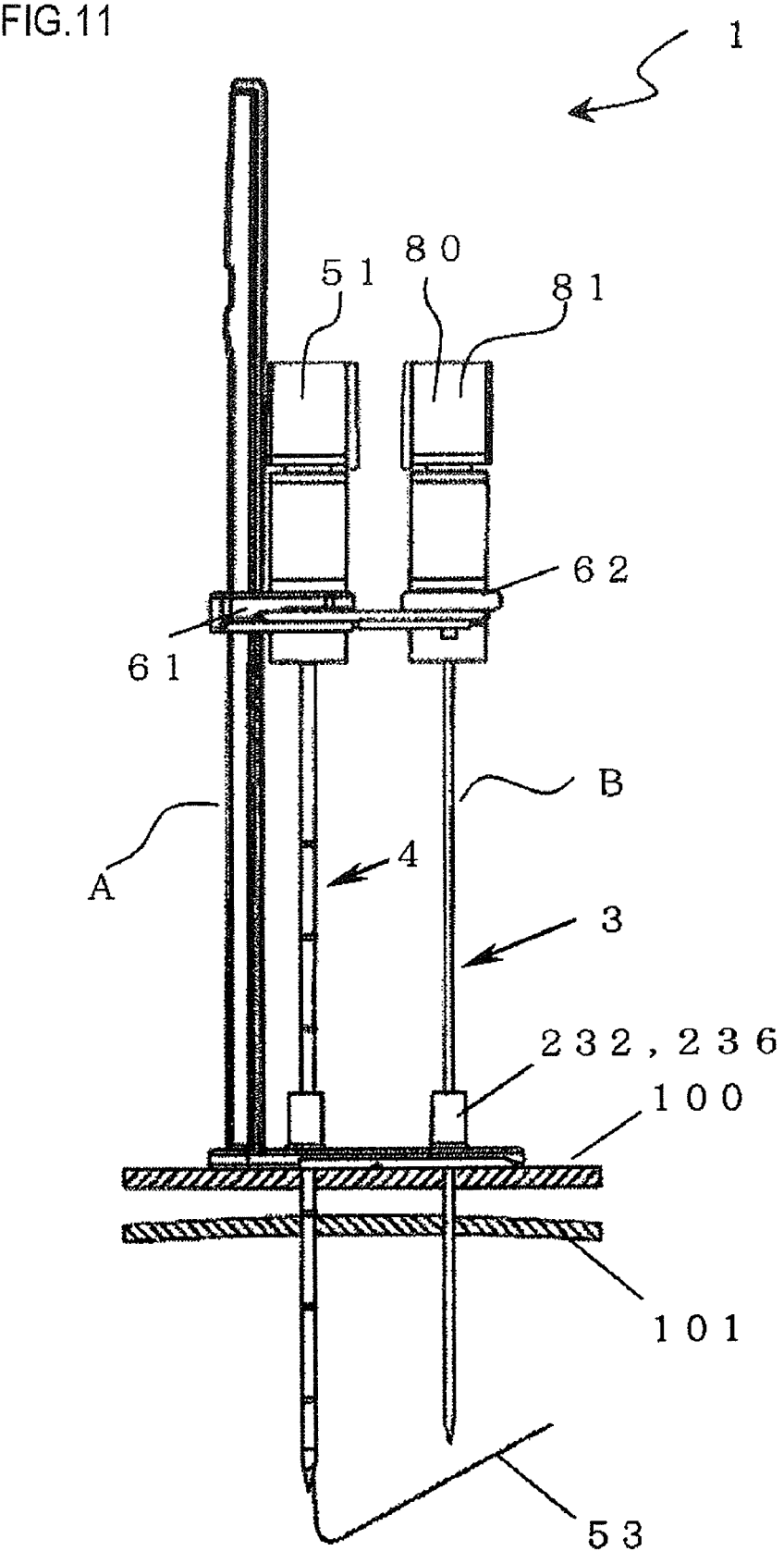
FIG. 11 is a front view showing a state in which the second puncture needle is inserted.

As shown in FIG. 11, the second holding plate 62 accompanying the second puncture needle 3 inserted into the second guide hole 236 separably abuts on the first holding plate 61 accompanying the first puncture needle 4 from above in the medical device 1 according to this embodiment, as will described below in detail.

Figure 16:
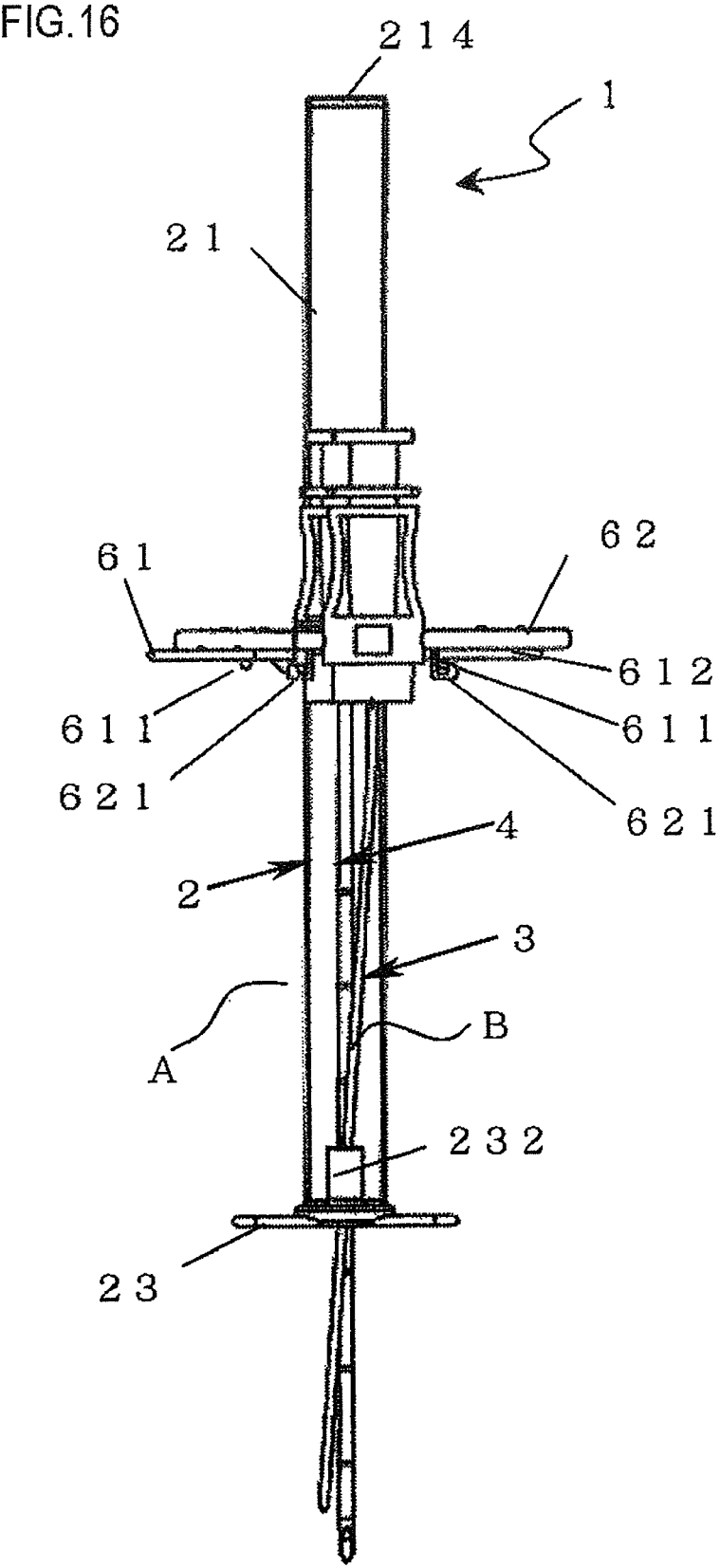
FIG. 16 is a right side view showing a state in which the second holding plate of the pulled-out medical device is slid toward the first wing and fitted.

As shown in FIGS. 16 and 17, the first holding plate 61 and the second holding plate 62 include a convex portion 611 and a concave portion 621 serving as a connector connected to each other. In a state in which the first holding plate 61 and the second holding plate 62 are connected to each other by connecting the convex portion 611 to the concave portion 621, the second puncture needle 3 is not perpendicular to but inclined with respect to the accommodation section 23. Therefore, the first puncture needle 4 and the second puncture needle 3 are in a state of not overlapping at least partially when the first puncture needle 4 is viewed from the second puncture needle 3 in the horizontal direction connecting the second guide hole 236 to the first guide hole 235. In this embodiment, upper end sides of the first puncture needle 4 and the second puncture needle 3 are displaced from each other in a direction crossing the horizontal direction.

The convex portion 611 and the concave portion 621 function as engagement unit constituting the connector. In this embodiment, an instance in which the concave portion provided on one of the first holding plate 61 and the second holding plate 62 and the convex portion provided on the other plate constitute the connector is shown. Alternatively, another engagement unit may constitute the connector.

FIGS. 16 and 17 show an instance in which the first holding plate 61 is connected to the second holding plate 62 by the convex portion 611 and the concave portion 621 in the direction orthogonal to the vertical direction.

Furthermore, the accommodation section (guide section) 23 is configured to include a cylindrical first accommodation section 231 in which the first guide hole 235 is formed, and a cylindrical second accommodation section 232 in which the second guide hole 236 is formed. The second accommodation section 232 including the second guide hole 236 is provided selectively in the horizontal direction of the accommodation section 23.

The cylindrical second accommodation section 232 in which the second guide hole 236 is formed according to this embodiment functions as a slider sliding along the accommodation section (guide section) 23 in the horizontal direction.

The second accommodation section 232 may continuously slide along the accommodation section 23 so that a position of the second accommodation section 232 is selectable. Alternatively, a plurality of latches may be discretely provided on the accommodation section 23, and the second accommodation section 232 may be arbitrarily selected from among finite and plural portions for the accommodation section 23 so that the position of the second accommodation section 232 is adjustable.

As shown in FIG. 1, the second accommodation section (slider) 232 is movable to an arbitrary position within a predetermined range on a slide groove 241 provided in the accommodation section 23. After moving the second accommodation section 232 to the arbitrary position, a stopper (fixing unit), not shown, can fix the second accommodation section 232 onto the accommodation section 23. This makes a position at which the second puncture needle 3 is inserted selectable within a range of a distance of the slide groove 241. A mechanism of the stopper is not limited to a specific one as long as the mechanism provides a method capable of easily fixing the second accommodation section 232 such as a screw mechanism or a fitting mechanism.

The main body 2 includes a locking section 212 locking the first puncture needle 4 in a state in which a tip of the first puncture needle 4 is accommodated in the first accommodation section 231. The locking section 212 locks the first puncture needle 4 when the first holding plate 61 is connected to the second holding plate 52 by the convex portion 611 and the concave portion 621, thereby accommodating a tip of the second puncture needle 3 in the second accommodation section 232.

A support member 21 includes a guide surface 213 provided on a tip side of the locking section 212.

The guide surface 213 is provided on a distal end side of a slide section 211 and closer to a tip end side of the slide section 211 than the locking section 212. The guide surface 213 is shaped so that a diameter of a slide surface of the slide section 211 is enlarged toward the locking section 211 and then reduced.

A slide hole 224 is formed in the first holding plate 61 so that the first unit A and the main body 2 move slidably with respect to each other. The locking section 212 is formed on the main body 2 as a concave portion with which the first holding plate 61 sliding in the slide hole 224 is disengageably engaged.

The slide section 211 is a portion that makes the first holding plate 61 slidable to be able to move forward or backward with respect to the support member 21. By moving the first holding plate 61 forward or backward, a piercing depth of the first puncture needle 4 is adjusted.

Figure 8A:
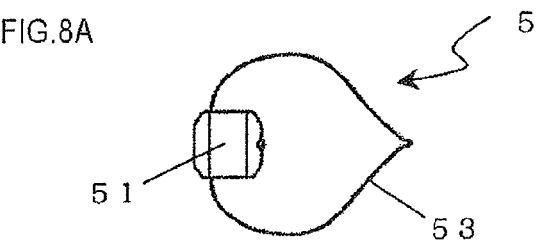
FIG. 8A is a top view of the suture traction tool.
Figure 8B:
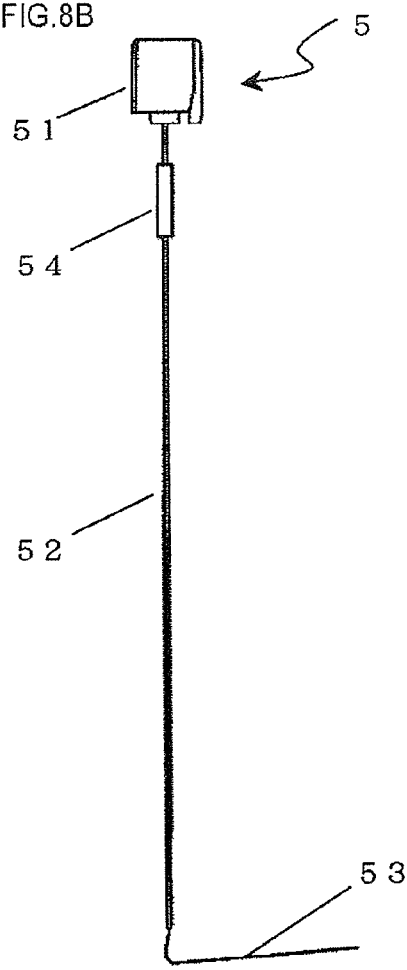
FIG. 8B is a front view of the suture traction tool.
Figure 8C:
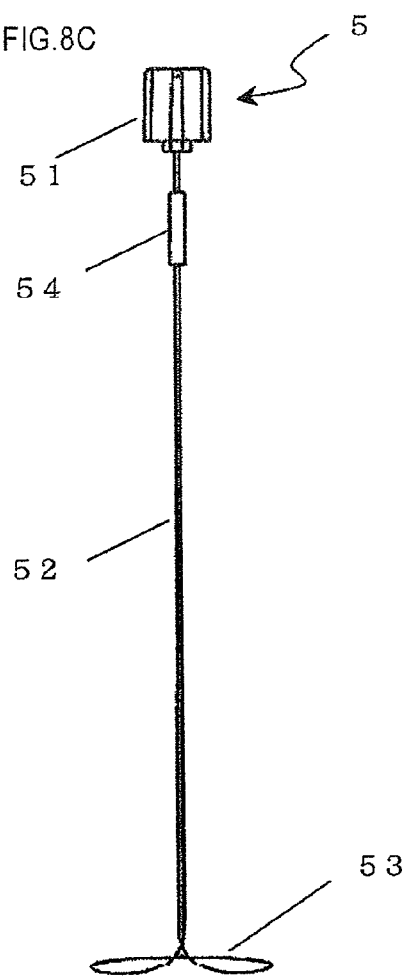
FIG. 8C is a right side view of the suture traction tool.

As shown in FIG. 8, the medical device 1 according to this embodiment further includes a suture traction tool 5. This suture traction tool 5 includes a rod section 52 slidably arranged within the first puncture needle 4, a handle section 51 formed integrally on an upper end of the rod section 52 and located upward of the upper end of the first puncture needle 4, and an annular section 53 that is a snare formed integrally on a lower end of the rod section 52 and protruding or retracting from the lower end of the first puncture needle 4.

The suture traction tool 5 is inserted into the first puncture needle 4 and functions to grasp the suture inserted from the second puncture needle 3 in the internal tissue and to pull the suture up to the body surface part. It is thereby possible to easily suture the body surface part to the internal tissue.

The annular section 53, which is made of a high elastic wire, is slidably movable within the first puncture needle 4 in a state of being linearly compressed. The annular section 53 expands annularly when protruding from the lower end of the first puncture needle 4.

As shown in FIGS. 1 and 2, the annular section 53 is formed so that a central axis or an extension of the central axis of the second puncture needle 3 penetrates through an interior of the annular section 53 in a state in which the annular section 53 protrudes from the first puncture needle 4. It is thereby possible to ensure that the annular section 53 can grasp the suture.

A diameter of the annular section 53 is not limited to a specific value. However, the annular section 53 is preferably formed so that the diameter thereof is equal to or larger than 1.5 L mm and equal to or smaller than 3.0 L mm if a distance between the second puncture needle 3 and the first puncture needle 4 is L mm. If the diameter is within the range, the annular section 53 has particularly superior performance of grasping the suture.

Furthermore, as shown in FIG. 8B, it is preferable that the suture traction tool 5 includes an insertion protection tube 54. By providing the insertion protection tube 54, even if the annular section 53 erroneously comes off, the annular section 53 can be easily made linear and inserted into the first puncture needle 4 when the annular section 53 is inserted into the first puncture needle 4 again. It is preferable that this insertion protection tube 54 has dimensions so that the insertion protection tube 54 can be contained in a hub 41 provided on the upper end of the first puncture needle 4 (see FIG. 7) and so that the insertion protection tube 54 can enter the second puncture needle 42. It is preferable that the rod section 52 has a length equal to or larger than a length when the annular section 53 is made linear.

Moreover, the medical device 1 includes the main body 2, the first holding plate 61 provided to be slidable with respect to the main body 2, and the first puncture needle 4 held by the first holding plate 61. The second holding plate 62 can be mounted on the first holding plate 61.

Furthermore, the second holding plate 62 is provided detachably from the first holding plate 61. Further, the second holding plate 62 is provided to be freely movable in a predetermined region on the first holding plate 61.

The second holding plate 62 is mounted on the first holding plate 61 so as to be adjusted to a generally elliptic outer edge of the first holding plate 61. It is thereby possible to keep a shape that an opening of the needle tip of the first puncture needle 4 faces that of the second puncture needle 3 (FIG. 1B).

Moreover, the convex portion 611 and the concave portion 621 are provided on the first and second holding plates 61 and 62, respectively (FIGS. 4B and 5B).

The convex portion 611 and the concave portion 621 are the engagement unit for engaging the second holding plate 62 with the first holding plate 61 by moving the second holding plate 62 to a first wing 612 of the first holding plate 61. In a state of connecting the first holding plate 61 to the second holding plate 62, the first puncture needle 4 and the second puncture needle 3 are in the state of not completely overlapping each other when being viewed from the second puncture needle 3-side horizontal direction of the accommodation section 23.

Furthermore, the accommodation section 23 includes the first and second accommodation sections 231 and 232 that accommodate therein the needle tips of the first puncture needle 4 and the second puncture needle 3, respectively (FIG. 1A).

The locking section 212 is provided on a proximal end side of the main body 2. If the first holding plate 61 engaged with the second holding plate 62 is slide to the proximal end side of the main body 2 and locked to the locking section 212, the first puncture needle 4 and the second puncture needle 3 are accommodated in the first and second accommodation sections 231 and 232, respectively (FIGS. 3A and 3B).

It is thereby possible to maintain the state in which the tips of the sharp needles are accommodated in the respective accommodation sections when the used medical device according to this embodiment is disposed of. It is, therefore, possible to prevent a secondary accident of erroneous insertion of the needle into a medical staff member. Further, when the tips of the two puncture needles are accommodated in the respective accommodation sections, the second holding plate 62 is moved to be closer to the first wing 612 of the first holding plate 61. By doing so, the second puncture needle 3 is in the state of not overlapping the support member 21 and the first puncture needle 4 at least partially when being viewed from the horizontal direction. It is thereby possible to visually recognize that the medical device 1 has been already used.

In the medical device 1 according to this embodiment, in the state in which the first holding plate 61 is connected to the second holding plate 62, the distance between the first puncture needle 4 and the second puncture needle 3 on the first or second holding plate 61 or 62 is smaller than the distance between the first puncture needle 4 in the first guide hole 235 and the second puncture needle 3 in the second guide hole 236 at a closest position to the first guide hole 235.

By so setting, the first puncture needle 4 and the second puncture needle 3 are assembled together to spread toward a lower end by connecting the first and second holding plates 61 and 62 to each other. Therefore, even if the medical device 1 is to be used, the second puncture needle 3 is inclined with respect to the second accommodation section 232 when being viewed from the second puncture needle 3-side horizontal direction of the accommodation section 23. That is, the second puncture needle 3 cannot be inserted after being inserted into the second guide hole 236 since a direction in which the second puncture needle 3 extends crosses a penetration direction of the second guide hole 236.

The accommodation section 23 also functions to accommodate therein the tips of the both puncture needles and, at the same time, to improve stability of using the medical device 1 since the accommodation section 23 abuts on the body surface part during manipulation.

The second accommodation section 232 functions to not only accommodate therein the needle tip but also improve stability when the second puncture needle 3 is inserted. That is, because of the cylindrical second accommodation section 232, it is possible to stably insert the second puncture needle 3 without oscillation by inserting the second puncture needle 3 along an interior of the cylindrical shape of the second accommodation section 232.

A method of fixing a gastric wall to an abdominal wall, that is, one method of using the medical device according to this embodiment will next be described with reference to FIGS. 9 to 17.

Prior to use the medical device 1 according to this embodiment, an operator inserts an endoscope into a stomach of a patient that is a living body, feeds sufficient air into the stomach, and closely attach an abdominal wall 100 to a gastric wall 101. Next, the operator checks a position of the stomach by a transmitted light by the endoscope, palpates an abdomen of the patient from a body surface part-side, decides a region to the gastric wall is fixed, disinfects an abdominal skin that is a body surface, and gives a local anesthetic to the patient.

Figure 9:
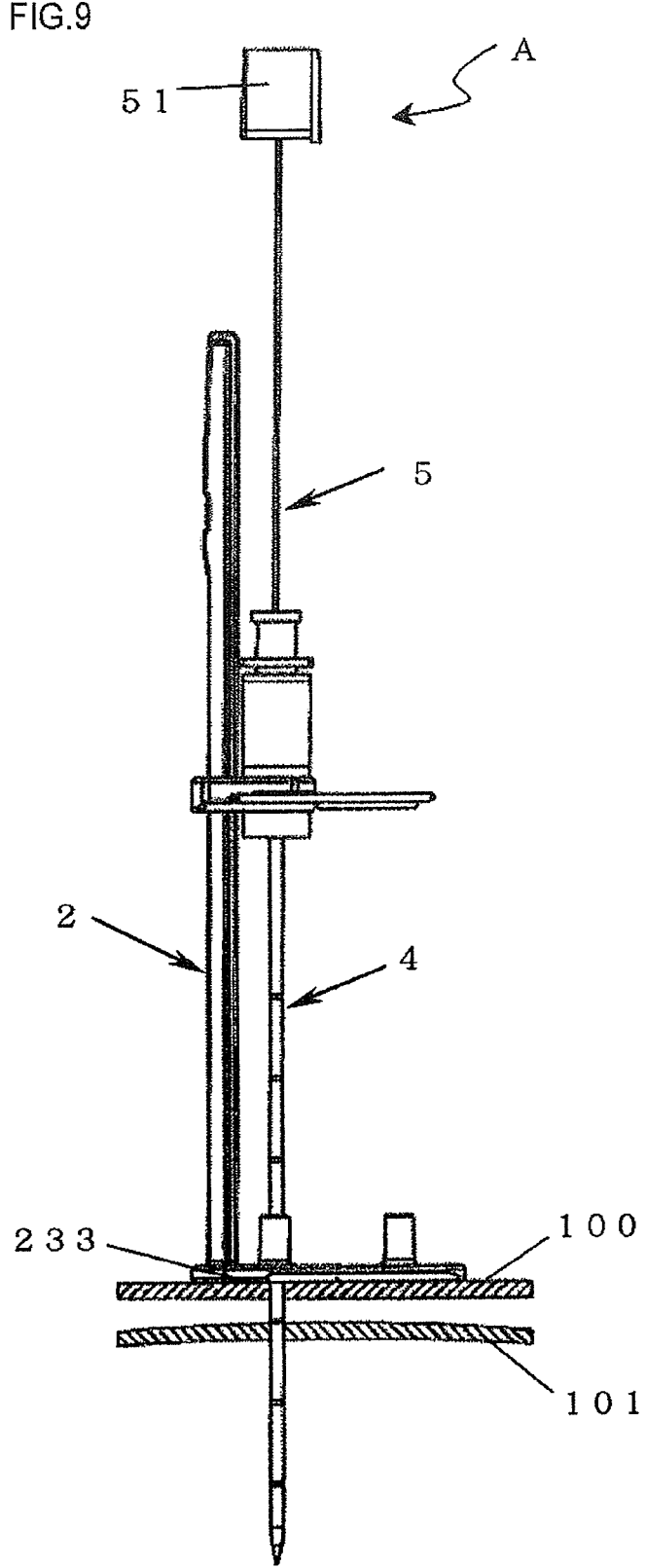
FIG. 9 is a front view showing a state in which the first puncture needle is inserted from an abdominal wall to a gastric wall.

Next, as shown in FIG. 9, the operator abuts an abutment section 233 of the main body 2 on the abdominal wall 100, slidably moves the first puncture needle 4 downward of the main body 2, and inserts the needle into the stomach from the body surface.

The operator inserts the first puncture needle 4 into the stomach while keeping the annular section 53 of the suture traction tool 5 in a state of being accommodated in the first puncture needle 4. By doing so, it is possible to protrude or retract the annular section 53 from the tip of the first puncture needle 4 right after insertion of the first puncture needle 4.

Figure 10:
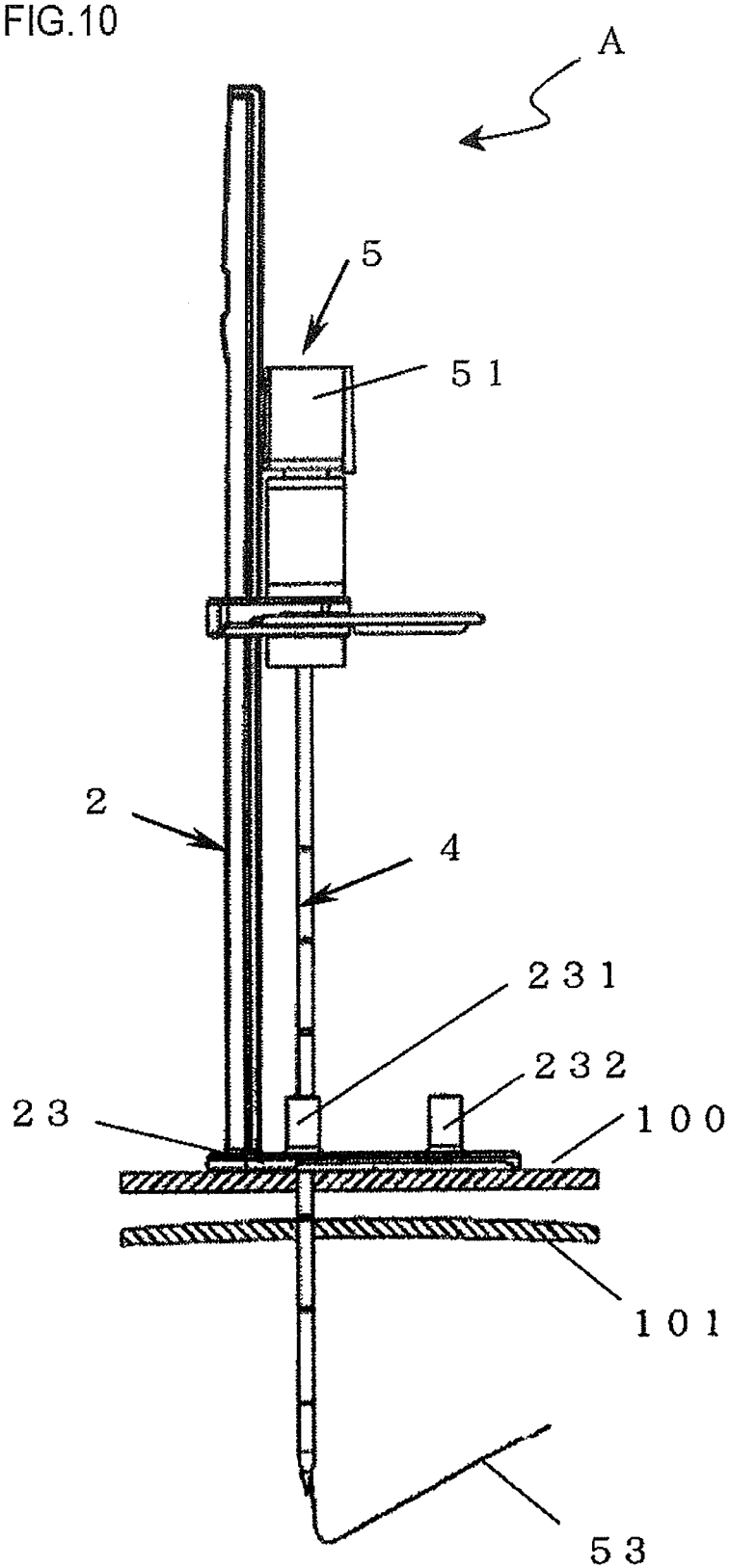
FIG. 10 is a front view showing a state in which an annular section of the suture traction tool is protruded from the tip of the first puncture needle.

Next, as shown in FIG. 10, the operator manipulates the handle section 51 of the suture traction tool 5, slidably moves the annular section 53 accommodated in the first puncture needle 4 downward, and protrudes the annular section 53 into the stomach. The operator rotates the accommodation section 23 as well as the main body 2 about the inserted first puncture needle 4 used as a central axis to be moved to a desired position if necessary, moves the second accommodation section 232 to adjust a distance between the second accommodation section 232 and the first accommodation section 231, and decides a piercing position of the second puncture needle 3. The piercing position of the second puncture needle 3 can be appropriately selected from within a range of 360 degrees about the first puncture needle 4 and within a range in which the second accommodation section (slider) 232 is slidable in the horizontal direction along the slide groove 241 provided in the accommodation section 23.

The range within which the second accommodation section (slider) 232 slides with respect to the accommodation section (guide section) 23 in the horizontal direction is not limited to a specific range. Specifically, it is preferable that the range includes at least a region where a distance between central portions of the second guide hole 236 and the first guide hole 235 is equal to or larger than 5 mm and equal to or smaller than 25 mm. The operator can thereby insert the second puncture needle 3 into the second accommodation section 232 slidably moved to a desired position, and select an optimum distance by which the abdominal wall is sutured to the gastric wall.

It is also preferable that a scale 238 (see FIG. 1A) is printed on one surface, for example, an upper surface of the accommodation section 23 so that the operator can check the distance from the first puncture needle 4 to the second puncture needle 3 on the body surface. The scale 238 indicates the distance between the first puncture needle 4 inserted into the first guide hole 235 and the second puncture needle 3 inserted into the second guide hole 236 in the accommodation section (guide section).

By printing this scale 238 on the upper surface of the accommodation section 23, the operator can check the distance by which the gastric wall is fixed to the abdominal wall.

It is further preferable that an indicator 55 indicating a distance from a longitudinal axis of the rod section 52 of the suture traction tool 5 is printed on the annular section 53. That is, the indicator 55 that indicates the distance from the first guide hole 235 into which the rod section 52 is inserted in the horizontal direction is printed on the annular section 53 by Roman characters or the like. By doing so, the operator can insert the second puncture needle 3 into an optimum position if selecting the position into which the second puncture needle 3 is inserted from within the stomach using the endoscope. This is because the operator can move the second guide hole 236 outside the body according to the distance indicated by the indicator 55 observed by the endoscope.

As shown in FIG. 11, the operator inserts the second puncture needle 3 into the second guide hole 236 of the accommodation section 23 slidably moved to the desired position, and inserts the second puncture needle 3 into the body so as to be almost perpendicular to the abdominal wall 100 and the gastric wall 101 of the patient. The operator mounts the second holding plate 62 holding the second puncture needle 3 on the first holding plate 61. By operator's mounting the second holding plate 62 to be adjusted to the generally elliptic outer edge of the second holding plate 62, it is possible to keep both the openings of the needle tips of the second puncture needle 3 and the first puncture needle 4 in a direction where the openings face each other.

It is preferable that the operator can determine at a glance that when the operator mounts the second holding plate 62 on the first holding plate 61 the opening of the tip of the second puncture needle 3 is always in the same direction. For example, arrow labels or the like indicating the openings of the needle tips of the first puncture needle 4 and the second puncture needle 3 are bonded on an upper surface of the handle section 51 provided on the suture traction tool 5 and an upper surface of an inner needle handle section 81 provided on an inner needle 80, respectively. If the second holding plate 62 is mounted on the first holding plate 61 so as to make directions of the arrow labels identical, an attitude in which the openings of the needle tips of the first puncture needle 4 and the second puncture needle 3 face each other.

Another unit may be adopted in the medical device as long as the operator can visually determine the directions of the openings of the needle tips of the first puncture needle 4 and the second puncture needle 3 using the unit.

Figure 12:
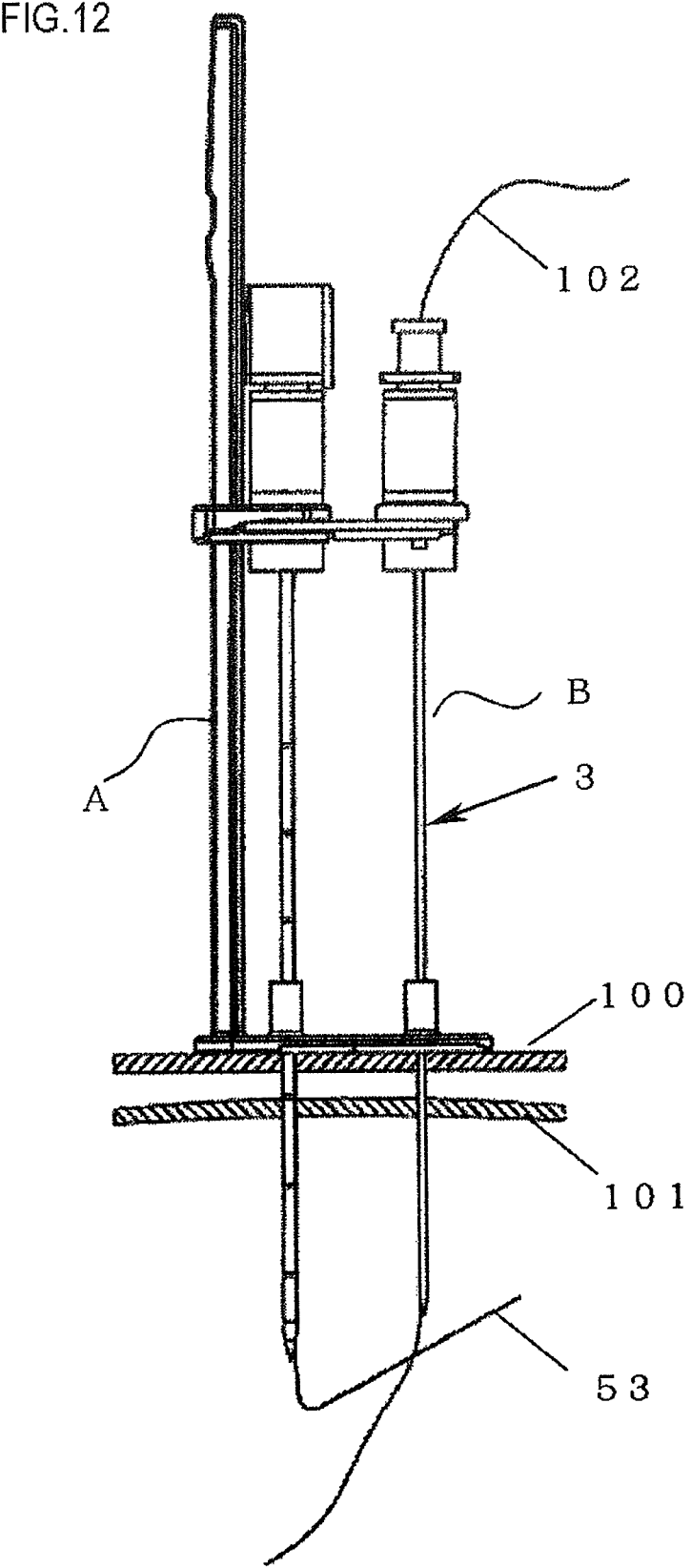
FIG. 12 is a front view showing a state in which a suture is inserted from the second puncture needle.
Figure 13:
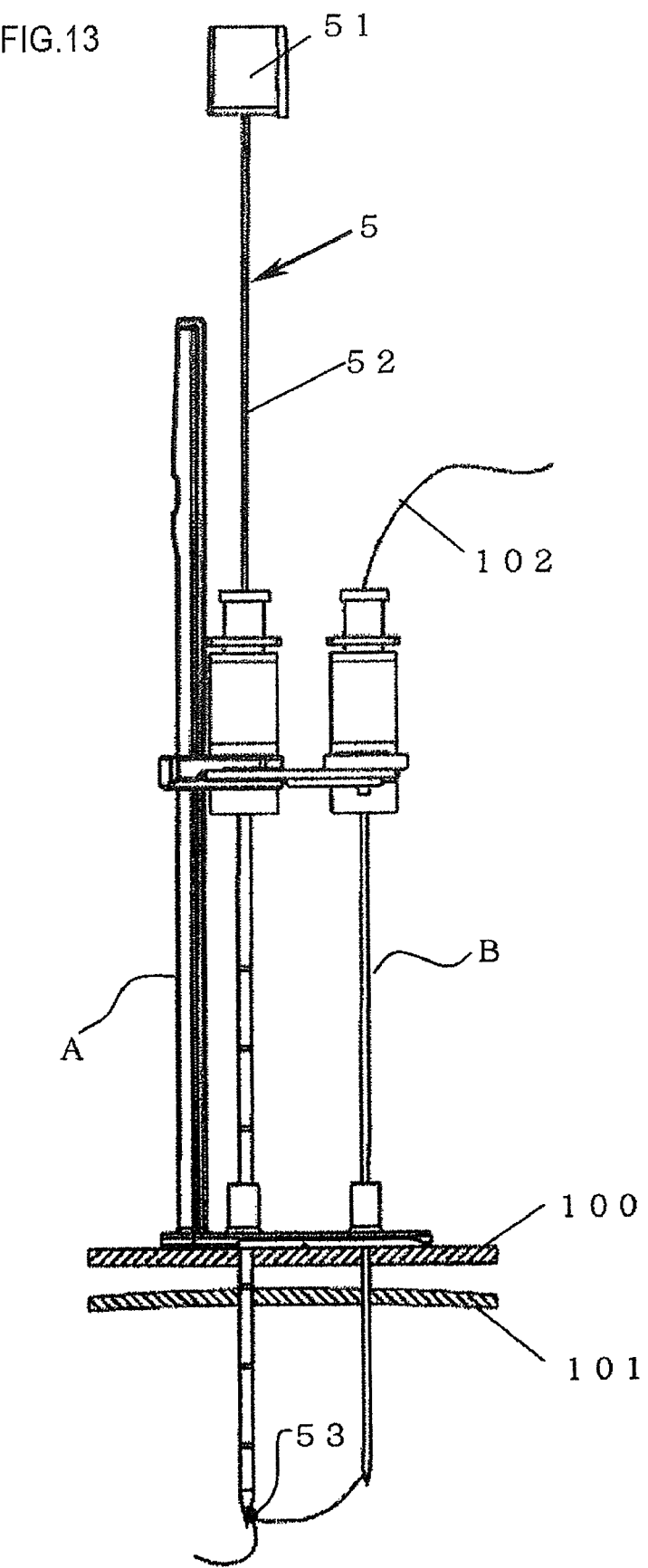
FIG. 13 is a front view showing a state in which the suture traction tool grasps the suture.

Next, as shown in FIG. 12, the operator pulls out the inner needle 80 from the second puncture needle 3, inserts a suture 102 into the second puncture needle 3 from an upper end of the second puncture needle 3, and protrudes the suture 102 from the needle tip. As shown in FIG. 13, the operator slidably moves the suture traction tool 5 upward, thereby causing the annular section 53 to grasp the suture 102.

Figure 14:
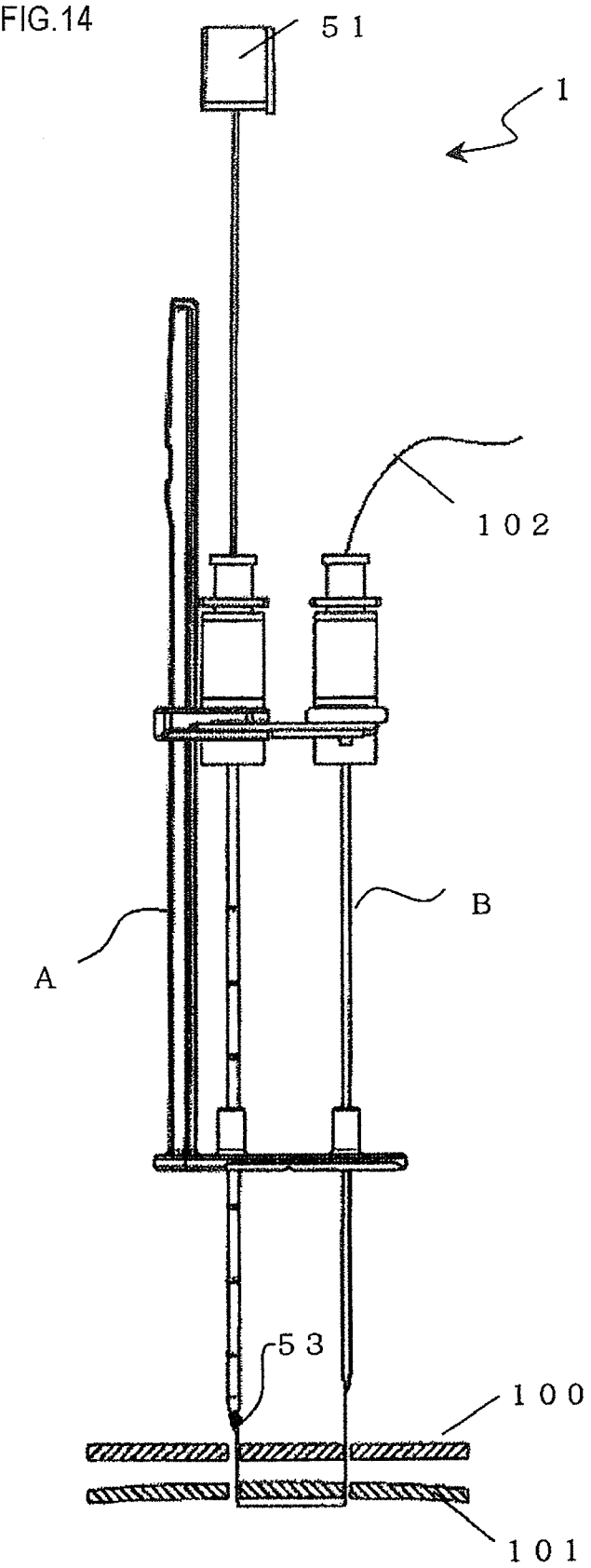
FIG. 14 is a front view showing a state in which the main body is pulled out from a patient.
Figure 15:
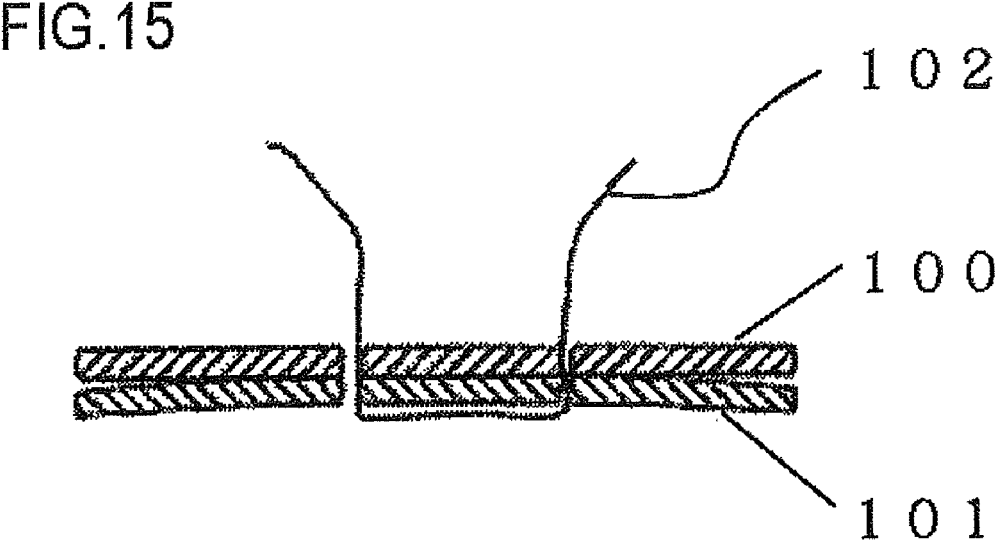
FIG. 15 is a front view showing a state in which both ends of the suture are exposed to a body surface from an interior of internal organs.

In such a state, the operator pulls the entire medical device 1 upward and simultaneously pulls out the first puncture needle 4 and the second puncture needle 3 to the outside of the body as shown in FIG. 14. As a result, both ends of the suture 102 are in a state of protruding from an interior of the stomach to the body surface as shown in FIG. 15. Therefore, the operator puts in this suture 102 on the body surface, thereby making it possible to fix the gastric wall to the abdominal wall.

After fixedly suturing the abdominal wall 100 to the gastric wall 101, the operator forces the second holding plate 62 into the first wing 612 of the first holding plate 61. The concave portion 621 provided on the second holding plate 62 is thereby fitted into the convex portion 611 provided on the first holding plate 61. This makes the first and second holding plates 61 and 62 into a state in which the first and second holding plates 61 and 62 are fitted into each other.

At this time, the second puncture needle 3 is not parallel to but inclined with respect to the first puncture needle 4 and the support member 21 (FIG. 16). Due to this, the operator can visually check that the medical device 1 is a used instrument. In addition, even if the operator is to use the medical device 1 in such a state, the operator cannot insert the second puncture needle 3 since the second puncture needle 3 is inclined with respect to the penetration direction of the second guide hole 236.

The operator forces a manipulation section 214 of the support member 21 of the main body 2 into the tip side (FIG. 16), changes over a state to a state of accommodating the sharp tips of the first puncture needle 4 and the second puncture needle 3 into first accommodation section 231 and the second accommodation section 232, and disposes of the medical device 1.

Figure 17A:
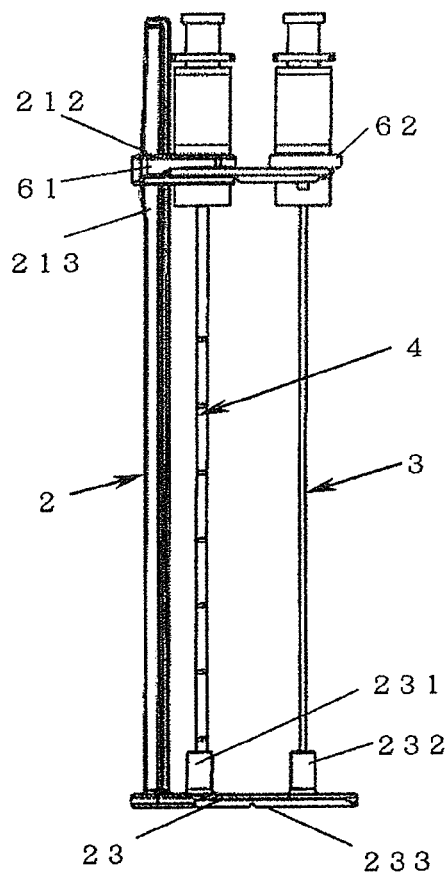
FIG. 17A is a front view showing a state in which the tips of the puncture needles of the medical device are accommodated into the main body.
Figure 17B:
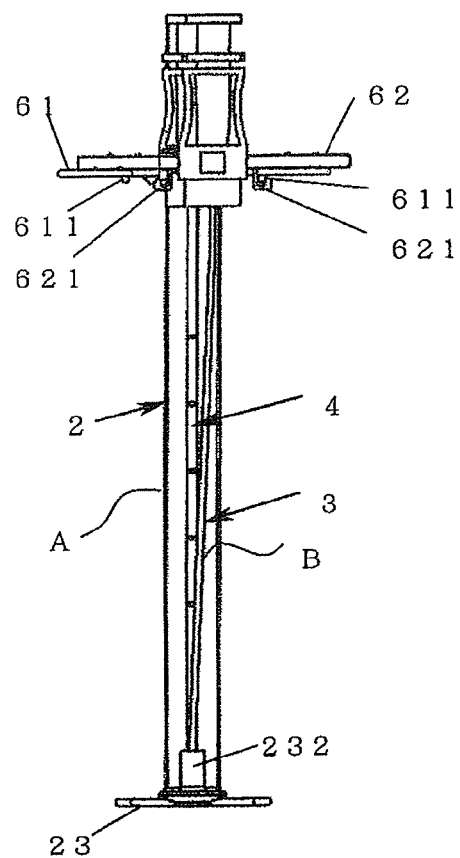
FIG. 17B is a right side view showing the state.

By carrying out the above-stated operation, the state of accommodating the needle tips into the accommodation sections can be kept. It is, therefore, possible to prevent a secondary accident of erroneous insertion of the needle into a medical staff member (FIGS. 17A and 17B). For example, the used medical device described in the above-stated Patent Document 1 is disposed of in a state in which the needle tips protrude, which possibly causes a secondary accident of erroneous insertion of the needle into the medical staff member.

As stated above, by using the medical device according to this embodiment, the sharp tips of the two puncture needles can be completely covered with the main body at the time of disposal of the medical device after suturing the abdominal wall 100 to the gastric wall 101. Due to this, the operator can safely dispose of the medical device 1 and visually confirm that the medical device 1 is a used instrument. It is, therefore, possible to prevent the secondary accident of erroneous insertion of the needle into a medical staff.

Moreover, in the state in which the first and second holding plates 61 and 62 are connected to each other, it is difficult to smoothly slidably move the first puncture needle 4 and the second puncture needle 3. It is, therefore, possible to ensure prevention of an erroneous operation that the first puncture needle 4 and the second puncture needle 3 are simultaneously inserted into the living body while the first and second holding plates 61 and 62 are connected to each other. Provided that the first puncture needle 4 and the second puncture needle 3 are inserted into the living body while the first and second holding plates 61 and 62 are connected to each other, the second puncture needle 3 is inserted into the living body in a state in which the second puncture needle 3 is enlarged obliquely. It is difficult to pull out the first puncture needle 4 and the second puncture needle 3 inserted into the living body in the state in which the second puncture needle 3 is enlarged obliquely from the living body. If the operator forcedly pulls out the first puncture needle 4 and the second puncture needle 3 from the living body, then the living body is possibly damaged and the patient possibly experiences great pain.

A failure that the above-stated erroneous operation causes the tips of the first puncture needle 4 and the second puncture needle 3 to be enlarged within the living body is more conspicuous if a distance from the body surface to the internal organ is longer such as thick fat under the skin.

In addition, when the second puncture needle 3 is inclined as described above, it may be difficult to grasp the suture 102 which protrudes from the tip of the second puncture needle 3 by the annular section 53 of the suture traction tool 5.

Besides, the internal organ such as the stomach into which the first puncture needle 4 and the second puncture needle 3 are inserted as stated above has an outer surface curved spherically. Due to this, if the first puncture needle 4 and the second puncture needle 3 are inserted into the internal organ simultaneously so as to obliquely enlarge the second puncture needle 3, then the first puncture needle 4 and the second puncture needle 3 are possibly not inserted thereinto smoothly and an outer surface of the internal organ is possibly damaged.

As stated so far, the medical device according to this embodiment has been described based on the mode of carrying out the invention. However, the present invention is not limited to the embodiment. For example, shapes of the support section, abutment section and the like of the main body, shapes of hubs of the second puncture needle (suture-insertion needle) and the first puncture needle (suture-grasping needle) and the like may differ from those according to the above-stated embodiment.

Figure 18A:
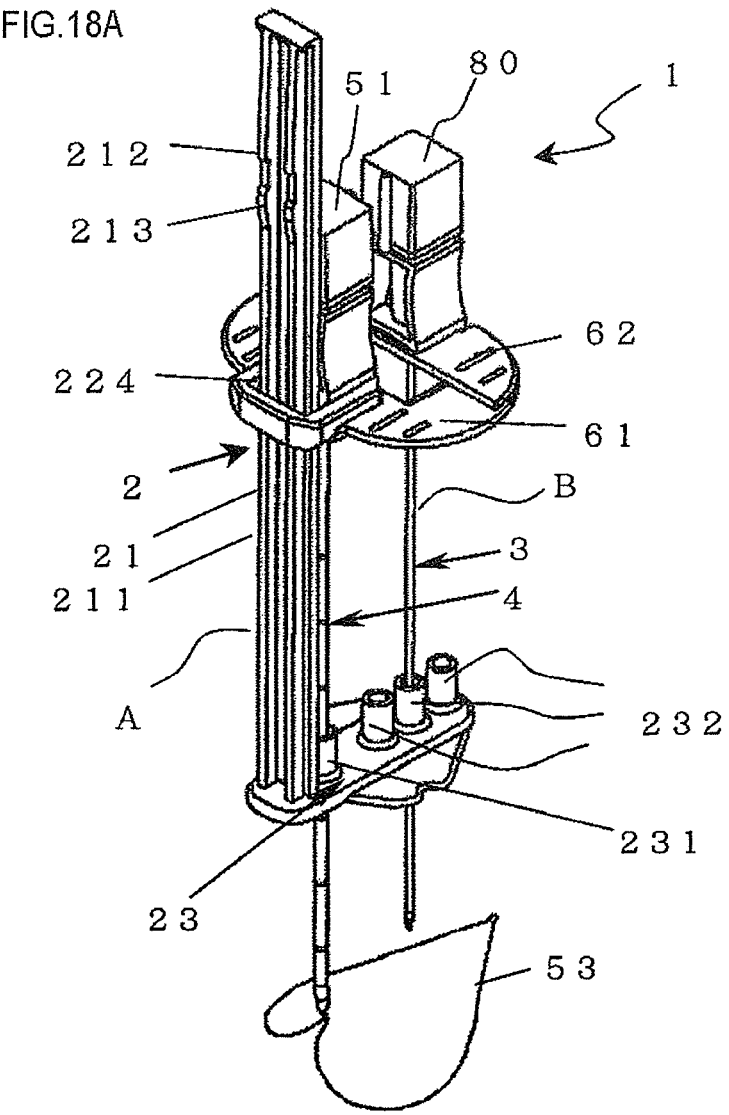
FIG. 18A is a perspective view showing a medical device according to another embodiment.
Figure 18B:
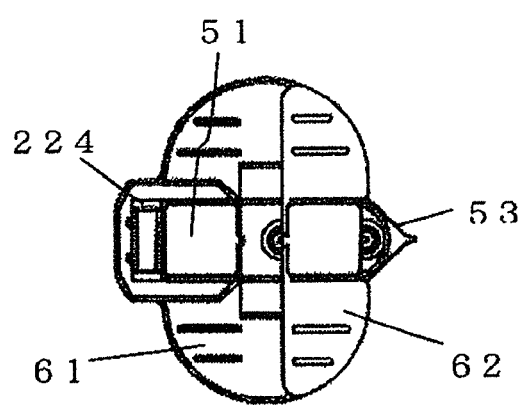
FIG. 18B is a top view of the medical device.
Figure 19:
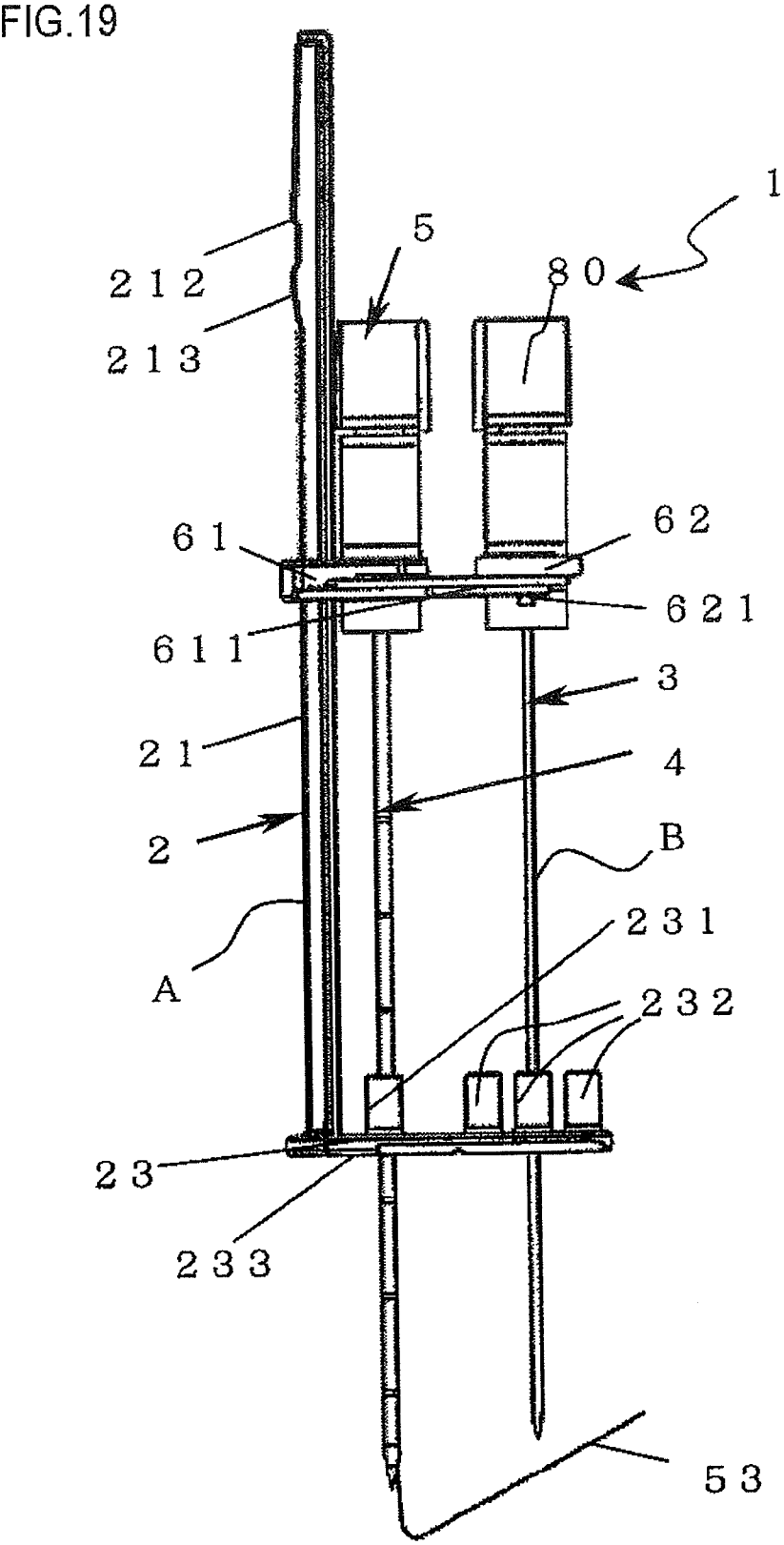
FIG. 19 is a front view of the medical device according to another embodiment.
Figure 20A:
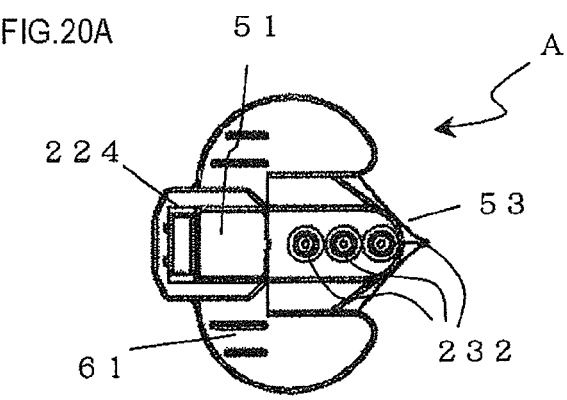
FIGS. 20A and 20B are a top view and a front view showing a state in which a main body of the medical device according to another embodiment, a first puncture needle, and a first holding plate are assembled together, respectively.
Figure 20B:
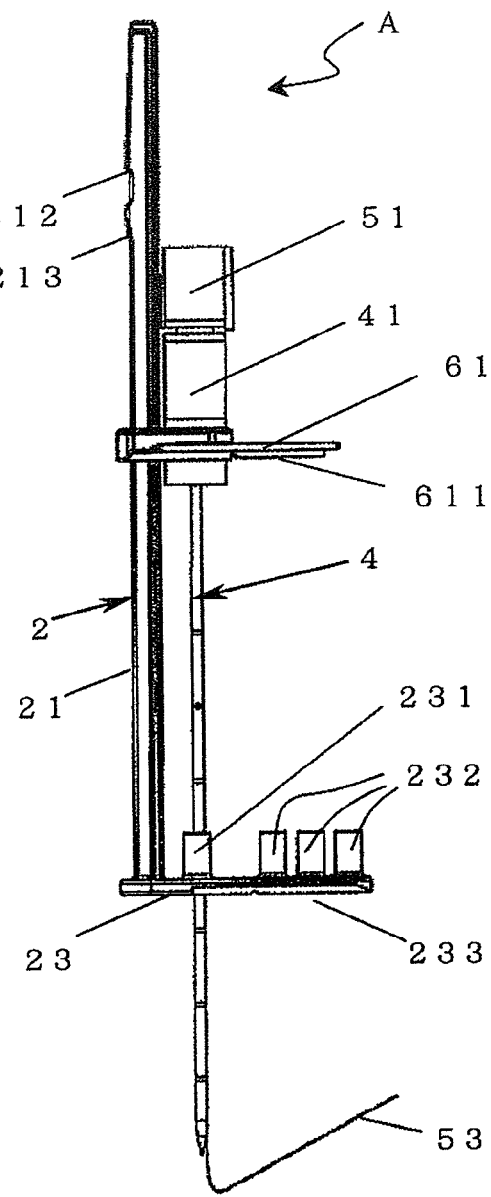

For example, another embodiment will be described with reference to FIGS. 18 to 20. This embodiment differs from the preceding embodiment in that at least two second guide holes 236 different in a distance to a first guide hole 235 are provided in an accommodation section (a guide section) 23. FIGS. 18 to 20 exemplarily show that three second accommodation sections 232 are provided in the accommodation section 23 in a horizontal direction.

By providing the three second accommodation sections 232 in the horizontal direction, it is possible to rotate the accommodation section 23 together with a main body 2 if necessary and to select a desired second guide section from among the three second accommodation sections 23 after insertion of a first puncture needle 4. By doing so, a second puncture needle 3 can be inserted into an optimum position.

It suffices that two or more second accommodation sections 232 are provided. If more second accommodation sections 232 are provided, a range of selecting a position into which the second puncture needle 3 is inserted can be made wider.

Furthermore, by providing a convex portion 611 on a first holding plate 61 and a concave portion 621 on a second holding plate 62, the first holding plate 61 can be engaged with the second holding plate 62 similarly to the preceding embodiment. In a medical device 1 according to this embodiment, the main body 2 includes a locking section 212 locking the first puncture needle 4 in a state of accommodating a tip of the first puncture needle 4 in a first accommodation section 231. When the first puncture needle 4 is locked to the locking section 212, a tip of the second puncture needle 3 connected to the first puncture needle 4 via the first and second holding plates 61 and 62 is accommodated in a second accommodation section 232.

Due to this, it is possible to prevent sharp needle tips of the first puncture needle and the second puncture needle of the used medical device from being exposed. It is, therefore, possible to safely dispose of the medical device with a simple structure.

In this way, in the medical device 1 according to this embodiment in which a plurality of second accommodation sections 232 is present, a selection range of a position into which the second puncture needle 3 is inserted is narrower than that according to the preceding embodiment. However, the accommodation section 23 can be made simpler structurally, operability for inserting the second puncture needle 3 can be improved, and the medical device 1 can be manufactured at low cost.

Furthermore, a method of connecting the first holding plate 61 to the second holding plate 62 according to this embodiment is a method by which the first puncture needle 4 does not overlap the second puncture needle 3 when being viewed in the horizontal direction from the second puncture needle 3 of the guide section in the state in which the first holding plate 61 is connected to the second holding plate 62 by a connector.

Moreover, the method of connecting the first holding plate 61 to the second holding plate 62 according to this embodiment is a method by which a distance between the first puncture needle 4 and the second puncture needle 3 on an upper end side on which the holding plates are provided is smaller than a distance between the first puncture needle 4 in a first guide hole 235 and the second puncture needle 3 in a second guide hole 26 at a proximate position to the first guide hole 235 up to a slidable limit in the state in which the first holding plate 61 is connected to the second holding plate 62 by the connector.

Portion of the living body where the medical device according to the present invention are used is not limited to the abdominal wall and the gastric wall but the medical device according to the present invention can be used to fix lift each internal organ wall, a blood vessel, a nerve or the like up to an abdominal wall. Moreover, the instance of fixing the internal organ of a human body has been exemplarily described in the embodiments, the medical device according to the present invention can be applied to a living body other than a human body.

The invention claimed is:
1. A medical device comprising:
a main body elongated in a vertical direction;
a guide section protruding from a lower end of said main body in a direction crossing said vertical direction, and including a first guide hole and a second guide hole penetrating through the guide section in said vertical direction;
a first unit including a first puncture needle of a hollow structure and a first holding plate, the first puncture needle being slidably supported by said main body near an upper end of the first puncture needle in the vertical direction and having a sharp lower end slidably inserted into said first guide hole from above, the first holding plate being integrally fixed to said first puncture needle at a position above the guide section; and
a second unit including a second puncture needle of a hollow structure and a second holding plate, the second puncture needle having a sharp lower end slidably inserted into said second guide hole from above, the second holding plate being integrally fixed to said second puncture needle at a position above the guide section, wherein
said first unit and said second unit are formed separately,
said second holding plate for said second puncture needle, when said second puncture needle is inserted into said second guide hole, separably abuts on said first holding plate for said first puncture needle from above,
the guide section further comprises a slider including said second guide hole, and
said slider is slidable along said guide section, such that a position of said second guide hole with respect to said first guide hole is selectable along said guide section.
2. The medical device as claimed in claim 1, wherein said slider slides within a sliding range including at least a region where a distance between a central portion of said second guide hole and a central portion of said first guide hole is equal to or larger than 5 mm and equal to or smaller than 25 mm.
3. The medical device as claimed in claim 1, wherein said guide section includes a slide groove slidably supporting said slider.
4. The medical device as claimed in claim 1, wherein said guide section includes a fixing unit for fixing said slidable slider.
5. The medical device as claimed in claim 1, comprising a connector separably connecting said first holding plate to said second holding plate, wherein
said slider is slidable in a direction connecting said second guide hole to said first guide hole, and
said first puncture needle to which said first holding plate is integrally fixed and said second puncture needle to which said second holding plate is integrally fixed are arranged in a non-parallel alignment when viewed along said slidable direction in a state wherein said first holding plate is connected to said second holding plate by said connector.
6. The medical device as claimed in claim 1, wherein a distance between said first puncture needle and said second puncture needle on said first or second holding plate is smaller than a distance between said first puncture needle in said first guide hole and said second puncture needle in said second guide hole located at a closest position to said first guide hole in a state of connecting said first holding plate to said second holding plate.
7. The medical device as claimed in claim 1, wherein a scale indicating a distance between said first puncture needle inserted into said first guide hole and said second puncture needle inserted into said second guide hole on said guide section is printed on one of surfaces of said guide section.
8. The medical device as claimed in claim 1, wherein said guide section includes a cylindrical first accommodation section having said first guide hole formed therein; and a cylindrical second accommodation section having said second guide hole formed therein,
said main body includes a locking section, said first puncture needle being locked to the locking section in a state of accommodating a tip of said first puncture needle in said first accommodation section, and
a tip of said second puncture needle connected to said first puncture needle locked to said locking section is accommodated in said second accommodation section.
9. The medical device as claimed in claim 8, wherein a slide hole for slidably moving said first unit and said main body with respect to each other is formed in said first holding plate,
said locking section is formed on said main body as a concave portion, said first holding plate sliding in said slide hole being locked to the concave portion.

10. The medical device as claimed in claim 1, further comprising a suture traction tool,
  wherein said suture traction tool includes:
  a rod section slidably arranged within said first puncture needle;
  a handle section formed integrally on an upper end of said rod section, and located upward of the upper end of said first puncture needle; and
  an annular section formed integrally on a lower end of said rod section, and protruding or retracting from the lower end of said first puncture needle.

11. The medical device as claimed in claim 10,
  wherein a distance from a longitudinal axis of said rod section is printed on said annular section.

* * * * *